United States Patent [19]

Bass

[11] Patent Number: 5,753,247
[45] Date of Patent: May 19, 1998

[54] METHOD OF TREATING FUNGAL INFECTIONS

[76] Inventor: James S. Bass, 12591 McGregor Blvd., Fort Meyers, Fla. 33919

[21] Appl. No.: 812,410

[22] Filed: Mar. 6, 1997

Related U.S. Application Data

[62] Division of Ser. No. 407,451, Mar. 20, 1995, Pat. No. 5,648,397.

[51] Int. Cl.$^6$ .............. A01N 25/00; A61K 31/13; A61K 31/70; A61K 31/56

[52] U.S. Cl. .............. 424/404; 424/400; 424/401; 424/405; 514/39; 514/169; 514/170; 514/200; 514/653

[58] Field of Search .............. 424/400, 401, 424/404, 405; 514/39, 169, 170, 200, 653

[56] References Cited

U.S. PATENT DOCUMENTS

| | | |
|---|---|---|
| 3,764,672 | 10/1973 | Argoudelis et al. .............. 424/181 |
| 4,226,850 | 10/1980 | Packman et al. .............. 424/47 |
| 4,568,343 | 2/1986 | Leeper et al. .............. 424/28 |
| 5,648,397 | 7/1997 | Bass .............. 514/653 |

*Primary Examiner*—Shelley A. Dodson
*Attorney, Agent, or Firm*—Sughrue, Mion, Zinn, Macpeak & Seas, PLLC

[57] ABSTRACT

Disclosed is a pharmaceutical composition intended for the topical application to human skin, comprising (A) as an effective ingredient, a mixture comprising (1) an antibiotic medication;

(2) an antihistamine; and (B) a physiologically acceptable carrier.

Also disclosed is a method for treatment using this composition.

16 Claims, No Drawings

5,753,247

1

METHOD OF TREATING FUNGAL INFECTIONS

BACKGROUND OF THE INVENTION

This is a divisional of application Ser. No. 08/407,451 filed Mar. 20, 1995, now U.S. Pat. No. 5,648,397.

The present invention is related to a topical composition which may be applied to skin for the purpose of killing fungus and/or bacteria or for the purpose of promoting hair growth.

Many fungicidal compositions are known in the art. But commonly their effectiveness in addressing fungal and/or bacterial infections in humans is quite limited. It appears in most instances that the human body's own immune system actually defends the infected area of the body, thereby reducing the amount of the antibacterial and/or fungicidal substances which pass through the barrier of the immune system and reach the infection. By reducing the free transfer of the disease from the affected area to the healthy areas, the body prevents or reduces the spread of the disease. But this function has the drawback of impeding the transfer of antibiotics and fungicides to affected areas where they may perform their function of killing the infection.

The present inventor has found that by suppressing the immune system, a freer transfer of antibiotics and/or fungicides can be achieved; the more the immune system is suppressed, the more effective the antibiotics and/or fungicides become.

Also, a number of compositions are known which are asserted to promote hair growth in humans. However, such hair growth compositions seem to work by stimulating blood flow and require constant application, suggesting that whatever hair growth results is forced. In other words, these compositions increase blood flow providing more nourishment for hair growth than occurred before the application of the compositions. Further, such compositions offer only limited success and only with a limited class of users.

Accordingly, an object of the present invention is to provide a composition which may be applied to human skin where it will successfully kill bacterial and/or fungal infections, without causing adverse side effects.

A further object of the present invention is to provide a composition which may be applied to human skin, particularly the head, where it will promote the growth of hair.

These and other objects are achieved by the present invention.

SUMMARY OF THE INVENTION

The present invention is a composition intended for the topical application to human skin, comprising
(1) an antibiotic medication such as penicillin VK (Rugby), doxycycline (Rugby) or erythrocin (Abbott Laboratories); and
(2) an antihistamine such as bromohenivamine (Schein), Chlorpromazine (Schein), diphenylhydramine hydrochloride (Parke-Davis), chlorpheniramine malate, chlorpromazine malate, and bromopheniramine.

Certain embodiments of the invention may also contain (3) an antiinflammatory medication such as aspirin (Goldline), hydrocortisone cream (Rugby), hydrocortisone powder (Parma-Tek Inc.) and hydrocortisone acetate injectable (Merck Sharp & Dohme), and/or (4) a bactericide combination of neomycin/bactracine polymyxin B sulfate.

The inventor has surprisingly found that this combination of ingredients produces remarkable effects in treating fungal and/or bacterial infections in humans and in promoting human hair growth.

DETAILED DESCRIPTION OF THE INVENTION

The human body's immune system builds a multifunctional defensive barrier between an affected area and an unaffected area of the body. The more dangerous the immune system considers this affected area to be, the more pronounced the interference between the affected and unaffected areas becomes. The ability to provide medication to the affected area is also reduced in direct relation to the effectiveness of this interference.

The present applicant has found that by temporarily reducing the effectiveness of this defensive area, ordinary medications become very effective very quickly. The composition described herein is intended to accomplish this result.

The composition described herein has been found to be effective in the treatment of conditions, such as dandruff, staph sores, fungal infections, urethra infection, scarring, and prostate infection.

Relative amounts of 50 to 80% by weight antihistamine to 50 to 20% by weight antibiotic/fungicide appear to be effective. Preferred relative amounts being 55 to 80% by weight antihistamine to 45 to 20% by weight antibiotic/fungicide, more preferred relative amounts being 60 to 75% by weight antihistamine to 40 to 25% by weight antibiotic/fungicide, and most preferred relative amounts being 65 to 75% by weight antihistamine to 35 to 25% by weight antibiotic/fungicide.

Although many combinations of types and brands of antihistamines and antibiotics and/or fungicides may be used effectively, antibiotics and fungicides which are known to work well with the particular infection to be treated, should be tried first.

It is desirable to mix the ingredients into a paste because a liquid is needed to carry the mixture of the invention into the affected area. The paste mixture should be kept moist to continue its effectiveness and to prevent undue drying of the mixture. If the paste mixture becomes unduly dry after application to the skin surface, it will tend to fall off the skin.

If the paste mixture is allowed to be dry on the skin, the addition of a cream may be helpful in holding the mixture together in place on the skin surface.

The best results appear to be obtained with hydrocortisone cream. The antiinflammatory characteristics of the cortisone are believed to aid in the free flow of the antibiotics. Topical compositions according to the present invention, which contain cortisone cream, virtually eliminate infections within a few hours to a few days. Also, pain and bruising is reduced with the use of cortisone cream.

The components of the present invention may also be combined with blephamide as a carrier. Embodiments of the invention containing blephamide result in particularly fast recovery, as well as offering good anaesthetic effects. Blephamide appears to be particularly effective in treating conditions on the eye lid or conditions effecting the surface of the skin such as burns.

The healing process with the topical composition of the present invention appears to be different from that with conventional compositions. While the healing period with the present invention may be 50 to 75% longer than with such conventional compositions, the pain, swelling, and discoloration associated with the infected area are greatly reduced. Scarring is also reduced and may actually be eliminated. Nerve regrowth is speeded up. Further, there is little or no scab growth because the body no longer regards the infected area as a location which must be protected.

The wound should be covered completely by the composition of the present invention throughout the first half of the healing process. Also, a portion of the area peripheral to the wound should be covered. For the remaining healing time, the wound itself should remain covered. If pain returns, full coverage should be restored.

Existing scars may be softened and reduced by application of the inventive composition.

The effective use of the present invention can be accelerated if the applied inventive composition is kept covered and moist.

The application of heat to the wound is also helpful.

Penicillin has been a widely prescribed antibiotic composition since the 1930's.

Diphenylhydramine is marketed in the United States under the name BENADRYL™.

Hydrocortisone is marketed in the United States under the name HYDROSKIN™.

The bactericide combination of neomycin/bactracine/polymyxin B sulfate is marketed in the United States under the name BACTINE™.

Turning to the use of the present invention for hair growth, the present inventor has concluded that hair growth compositions seem to work by stimulating blood flow and require constant application. This suggests that whatever hair growth results is forced growth. In other words, an increased blood flow provides more nourishment for hair growth than occurred before the application of these compositions. Further, such compositions offer only limited success and only with a limited class of users.

But with the composition of the present invention, one or more applications will grow hair in about eight weeks. Further, since no maintenance applications are required, the present inventor infers that the hair growth is not forced hair growth. Since the hair growth continues, even without further applications, for six months or more, the present inventor believes that the cause of such growth is an increase in nutrients which results in greater hair growth, rather than greater blood flow. The present inventor concludes that some forms of hair loss may be caused by infection(s) in the area of the hair follicle. The composition of the present invention reduces or kills such infection(s).

On the other hand, the infection(s) seem to return after a period of six months or more. Accordingly, new applications of the inventive composition are needed to maintain the hair.

The composition of the present invention also has the effect of reducing or treating dandruff. By varying the composition of the present invention, dandruff can be virtually eliminated as hair growth renews.

In some embodiments of the present invention, 10 grains of antibiotic and 10 grains of antihistamine are mixed together. To that mixture is added 6 to 12, or even more, grains of cream or ointment. If that cream or ointment is not cortisone cream, 3 or 4 grains of cortisone cream may be included. A liquid may be required at this point to achieve the proper consistency.

Injectable antihistamine and antiinflammatory preparations may be used. The addition of water or mineral oil to noninjectable antihistamine and antiinflammatory preparations is also effective in making paste of a workable consistency.

The present invention is further described by the following examples which should not be construed as limiting the scope of the invention in any respect.

EXAMPLE I

The powder from twelve 500 mg. penicillin tablets was combined with two 50 mg. ampules of injectable Benadryl™. Added thereto was about a 2½" to 3" squirt of Rugby Hydroskin™ and a few drops of Bactine™ until the mixture was thinner than honey.

This composition was then rubbed into a clean scalp at night and removed each morning for eight days. Within eight weeks hair growth was observed.

EXAMPLE II

A patient suffered a fungus infection under his toenails which had ridged them up to a considerable extent. On a clean toenail three applications of the composition of Example I brought back the pink skin under the nail. All of the white was gone.

EXAMPLE III

To a patient suffering from scar tissue behind his ear was subjected to repeated applications of the composition of Example I. Over an extended period of about three months, all of the scar tissue but one wrinkle and all of the effected flesh but one dot were gone.

What I claim is:

1. A method for treating a fungus infection in a human suffering from the fungus infection, said method comprising the step of applying a pharmaceutical composition intended for the topical application to human skin, said composition comprising (A) as an effective ingredient, a mixture comprising
      (1) an antibiotic medication;
      (2) an antihistamine; and
   (B) a physiologically acceptable carrier, wherein the antibiotic is present in a relative amount of 50% to 20% by weight and the antihistamine is present in a relative amount of 50% to 80% said amounts being based upon a total amount of antibiotic and antihistamine.

2. The method of treatment of claim 1, wherein the antiinflammatory medication is hydrocortisone cream.

3. The method of treatment of claim 1, wherein the mixture further comprises an antiinflammatory medication.

4. The method of treatment of claim 1, wherein the mixture further comprises a bactericide combination of neomycin/bactracine/polymyxin B sulfate.

5. The method of treatment of claim 1, wherein the antihistamine is bromopheniramine.

6. The method of treatment of claim 1, wherein the antihistamine is chlorpromazine.

7. The method of treatment of claim 1, wherein the antihistamine is diphenylhydramine hydrochloride.

8. The method of treatment of claim 1, wherein the antibiotic medication is penicillin VK.

9. The method of treatment of claim 1, wherein the antibiotic medication is doxycycline.

10. The method of treatment of claim 1, wherein the antibiotic medication is erythrocin.

11. The method of treatment of claim 1, wherein the antihistamine is bromohenivamine.

12. The method of treatment of claim 1, wherein the antihistamine is chlorpromazine.

13. The method of treatment of claim 1, wherein the antihistamine is diphenylhydramine hydrochloride.

14. The method of treatment of claim 1, wherein the antihistamine is chlorpheniramine malate.

15. The method of treatment of claim 1, wherein the antihistamine is chlorpromazine malate.

16. The method of treatment of claim 1, wherein the antihistamine is bromopheniramine.

* * * * *